(12) United States Patent
Roy et al.

(10) Patent No.: US 7,179,268 B2
(45) Date of Patent: Feb. 20, 2007

(54) DEVICE, APPARATUS, AND PROSTHESIS FOR SUTURLESS ANASTOMOSIS

(76) Inventors: Sumit Roy, Vækerøvn. 106, N-0383 Oslo (NO); Erik Fosse, Maridalsveien 71B, N-0458 Oslo (NO); Ole Jakob Elle, Fagerheimgata 36, N-0475 Oslo (NO)

( * ) Notice: Subject to any disclaimer, the term of this patent is extended or adjusted under 35 U.S.C. 154(b) by 557 days.

(21) Appl. No.: 10/333,746

(22) PCT Filed: Jul. 30, 2001

(86) PCT No.: PCT/NO01/00325
§ 371 (c)(1),
(2), (4) Date: Mar. 13, 2003

(87) PCT Pub. No.: WO02/09594
PCT Pub. Date: Feb. 7, 2002

(65) Prior Publication Data
US 2004/0102794 A1    May 27, 2004

Related U.S. Application Data

(60) Provisional application No. 60/222,051, filed on Jul. 31, 2000.

(51) Int. Cl.
*A61B 17/08* (2006.01)
(52) U.S. Cl. .................................................. 606/153

(58) Field of Classification Search ................. 606/99, 606/100, 153, 154–156; 128/207.14; 604/284; 623/1.1, 1.11, 1.12, 1.13, 1.16, 1.36, 23.64
See application file for complete search history.

(56) References Cited

U.S. PATENT DOCUMENTS

| | | | |
|---|---|---|---|
| 4,675,008 A * | 6/1987 | Tretbar | 604/284 |
| 5,893,886 A | 4/1999 | Zegdi et al. | 623/1 |
| 6,007,576 A * | 12/1999 | McClellan | 623/23.64 |
| 6,030,370 A | 2/2000 | Kupka et al. | 604/264 |
| 6,030,395 A | 2/2000 | Nash et al. | 606/153 |
| 6,165,185 A * | 12/2000 | Shennib et al. | 606/153 |
| 6,517,558 B2 * | 2/2003 | Gittings et al. | 606/153 |

FOREIGN PATENT DOCUMENTS

| | | |
|---|---|---|
| DE | 19704261 | 8/1998 |
| DE | 19725739 | 4/1999 |
| EP | 0824012 | 2/1998 |
| WO | WO99/48427 | 9/1999 |

OTHER PUBLICATIONS

Tulleken et al, NEUROCHIRURGICA, 1995, pp. 66-70, First Clinical Experience with Excimer Assisted High Flow Bypass . . .

* cited by examiner

*Primary Examiner*—Julian W. Woo

(57) ABSTRACT

The invention concerns a device for preparing a hollow organ for anastomosis to another hollow organ. The said device comprises an anastomosis prosthesis, deployment apparatus to deliver the said prosthesis to a desired site in the body and a coupling device to secure the said prosthesis to said deployment apparatus during delivery.

24 Claims, 13 Drawing Sheets

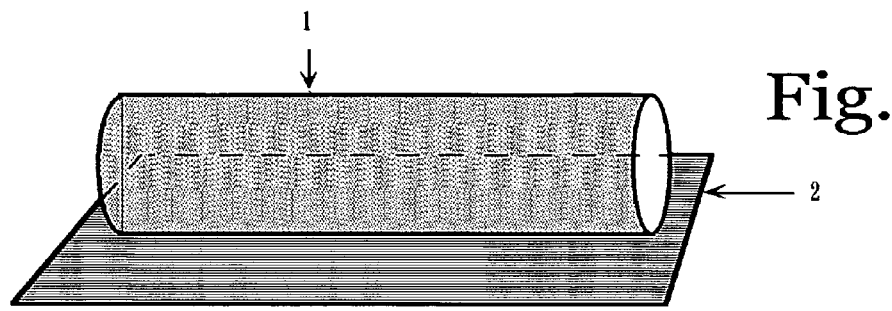
Fig. 5
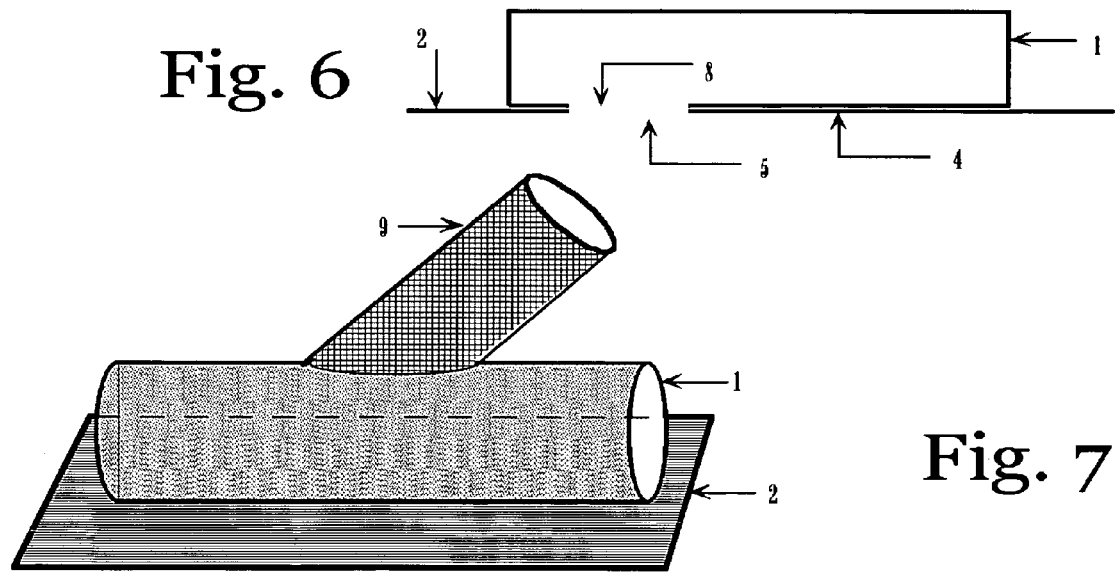
Fig. 6
Fig. 7
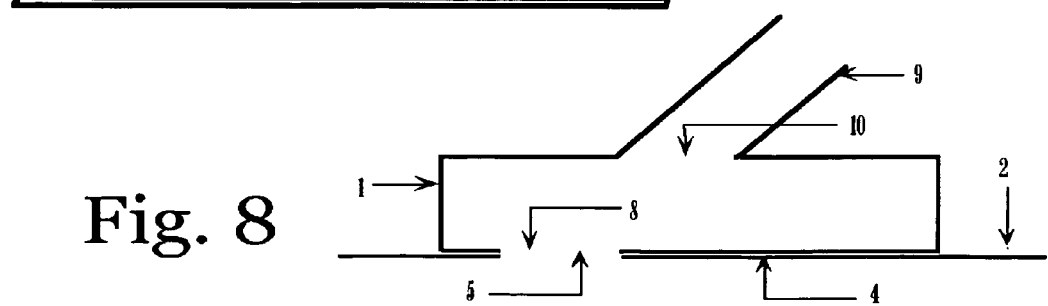
Fig. 8

DEVICE, APPARATUS, AND PROSTHESIS FOR SUTURLESS ANASTOMOSIS

RELATED APPLICATION

This is a nationalization of PCT/NO01/00325, filed Jul. 30, 2001 and published in English.

The patent application claims priority from U.S. Provisional Patent Application Ser. No. 60/222,051 filed on Jul. 31, 2000, the entire disclosure of the application being expressly incorporated herein by reference.

TECHNICAL FIELD

The invention disclosed in the patent application concerns a device for preparing a hollow organ for anastomosis to another hollow organ methods for using the said devices for the said purpose. The said device comprises an anastomosis prosthesis, deployment apparatus to deliver the said prosthesis to a desired site in the body and a coupling device to secure the said prosthesis to said deployment apparatus during delivery.

BACKGROUND ART

A simple method for joining one hollow organ end-to-side to another hollow organ, without interrupting fluid follow in the efferent organ has long been desired in the medical practice, particularly in the field of cardiovascular surgery. Conventional methods for joining (anastomosing) two blood vessels in an end-to-side configuration invariably necessitates halting blood flow in the efferent or outflow blood vessel, jepoardising the viability of tissues perfused by the outflow blood vessel. To overcome this drawback, a surgical technique has been described in medical literature that involves the stitching of a metal ring to the outflow vessel (Tulleken CAF, et. al. Acta Neurochir 1995; 134:66–70), and a tubular prosthesis to the inflow or afferent limb of the anastomosis. The later is stitched to the metal ring, and luminal continuity established with the help of optical energy transmitted by a catheter passed through the tubular prosthesis. The complexity of the procedure has hindered its adoption by surgeons.

Hence the use of a biocompatible adhesive instead of stitches has been advocated and devices exploiting the idea have been disclosed in PCT/NO99/00093.

The present invention extends this concept further by providing the means for implanting a prosthesis on a blood vessel without the need for manipulation of the blood vessel, making performance of remote-controlled, robot-assisted vascular anastomosis a clinically realistic proposition.

The coupling device comprises:
- a double-walled, substantially thimble-formed, ring shaped member consisting of at least one ring section, wherein each ring section comprises at least one radial partition walls defining at least two chambers, and a common upper chamber limited by a section roof, wherein the chambers are adapted for aposing to the anastomosis prosthesis and fastening to said prosthesis by means of a suction pressure, wherein the common upper chamber provides a channel in fluid connection with the chambers,
- a tubing connection assembly in fluid connection with said channel for transmitting a suction pressure from a suction apparatus to the chambers, and
- a fixation mechanism for fastening the ring shaped member to an anastomosis apparatus. The coupling device is thus meant for attachment to the prosthesis by suction, where the floor of the at least one section is apposed to the prosthesis.

There are several alternative ways of fastening the coupling device to the anastomosis apparatus, but all embodiments have the common feature that they permit easy, secure and precise fastening of these parts together.

In one embodiment of the invention, the coupling device is non-detachably attached to the deployment apparatus.

Back to the coupling device, in a first embodiment of the invention the coupling device comprises a fixation mechanism with:
- an attachment plate with a rectangular projection or offset block, the attachment plate and the offset block being perforated, and
- a threaded fixation pin through the attachment plate and the offset block, where the pin is provided on or in the vicinity of one end with a nut and on or in the vicinity of the other end with a fixation plate,
- where the offset block and the fixation plate are meant to be tightened against an outer and an inner surface respectively in a deployment tube in the apparatus by means of the pin.

In a second embodiment of the invention the fixation mechanism comprises:
- an attachment plate with a rectangular projection or offset block, and
- a fixation pin extending between the offset block and a fixation plate,
- where the offset block and the fixation plate are meant to be arranged against an outer and an inner surface respectively in a deployment tube in the apparatus.

In a third embodiment the fixation mechanism comprises:
- a torsion spring, where one limb of the torsion spring is attached to the fixation plate and the other limb is accommodated in a groove in the offset block,
- where the torsion spring is meant for pushing the fixation pin into a fixation slot in a deployment tube in the fixation apparatus.

In a fourth embodiment the fixation mechanism comprises a bent resilient wire in stead of a torsion spring, where one limb of the wire is attached to the fixation plate and the other limb is accommodated in a groove in the offset block, where the resilient wire is meant for pushing the fixation pin into a fixation slot in a deployment tube in the fixation apparatus.

In a fifth embodiment the fixation mechanism comprises:
- an attachment plate with a rectangular projection or offset block, and
- a polymer hook or loop patch bonded to the offset block,
- where the hook patch is meant for fastening the offset block to a corresponding polymer loop or hook patch on a deployment tube in the anastomosis apparatus.

In a sixth embodiment the fixation mechanism comprises:
- an attachment plate with a rectangular projection or offset block, and
- a flat magnet bonded to the offset block,
- where the flat magnet is meant for fastening the offset block to at least one corresponding ferromagnetic patch on a deployment tube in the anastomosis apparatus.

In a preferred embodiment of the invention the chambers are provided with a mesh on the surface adapted for aposing to the anastomosis prosthesis.

The deployment apparatus comprises:
- a targeting tube,
- a deployment tube provided with a fastening device for cooperation with a fixation mechanism in the prosthesis coupling device, for fastening said prosthesis coupling device to said deployment tube, a flow control valve for controlling fluid flow in and out of the apparatus, wherein the inlet of the valve is adapted for connection to a suction apparatus, and a first outlet of the valve is coupled to a fluid connecting device adapted for connection to a corresponding tubing connection assembly in the anastomosis coupling device, a flow control lever for controlling flow through said valve, and a trigger for displacing the deployment tube in relation to the body of the apparatus, a device for connecting the apparatus to a suction apparatus.

As one can see, the apparatus according to the invention has a targeting tube that permits a precise localisation of the apparatus at the anastomosis site, a deployment tube for receiving the coupling device and thus the prosthesis, and two triggering/control devices for controlling on one side suction pressure to be exerted by the coupling device against the anastomosis prosthesis and on the other side the movement of the prosthesis towards the anastomosis site. In one embodiment the targeting tube is adapted for applying suction to the organ to be anastomosed, thereby securing a stationary location of the apparatus. In another embodiment the apparatus is adapted for apposing the anastomosis prosthesis to the target organ with positive pressure.

In a first embodiment of the apparatus, adapted for use together with the first to fourth embodiments of the coupling device, the fastening device consists of at least one fixation slot extending from the edge of the deployment tube.

In a second embodiment of the apparatus, specially adapted for use together with the second embodiment of the coupling device each fixation slot comprises a long limb, a fixation fluke, a transverse limb and a short limb, where the fixation fluke is meant for securing a fixation pin in a fixation mechanism in the prosthesis coupling device into the short limb of the fixation slot.

In a third embodiment of the apparatus, specially adapted for use together with the third embodiment of the coupling device each fixation slot comprises a long limb, a transverse limb and a short limb, where the short limb is meant for receiving a fixation pin in a fixation mechanism in the prosthesis coupling device.

In a fourth embodiment of the apparatus, adapted for use together with the fifth embodiment of the coupling device the fastening device consists of at least one loop or hook polymer patch arranged on the deployment tube for fastening to a corresponding hook or loop patch in a fixation mechanism in the prosthesis coupling device.

In a fifth embodiment of the apparatus, adapted for use together with the sixth embodiment of the coupling device the fastening device consists of at least one ferromagnetic patch arranged on the deployment tube for fastening to a corresponding magnet in a fixation mechanism in the prosthesis coupling device.

In a preferred embodiment, the apparatus comprises an inlet for introduction of imaging or flow measuring devices.

As stated before, in another preferred embodiment of the invention the second outlet of the flow control valve is coupled to the inside of the targeting tube for transmitting a suction pressure to said targeting tube.

In another embodiment of the invention the coupling device is non-detachably attached to the deployment apparatus.

The implantable anastomosis prosthesis comprises a first tubular member to be placed around a first organ, and a flat sheet or attachment member to be placed on a second organ, wherein the luminal or inner surface of the tubular member is continuous with the surface of the flat member facing the second organ.

Use of the apparatus according to the invention will now be described briefly:

1) The coupling device is attached to the deployment tube,
2) the targeting tube is introduced into the side-arm of the anastomosis prosthesis,
3) the prosthesis is slid up the targeting tube till the prosthesis flat member abuts the coupling device,
4) the coupling device is fastened to the prosthesis,
5) the apparatus is introduced into the body and the tip of the targeting tube is placed at the chosen side for anastomosis,
6) the triggering device is pressed activating the actuator, and the deployment tube is longitudinally displaced along the targeting tube towards the organ, thereby delivering the mounted anastomosis prosthesis to the organ,
7) the anastomosis prosthesis is pressed against the organ,
8) the coupling device is detached from the anastomosis prosthesis.

The implantable anastomosis prosthesis is secured to the coupling device by establishing suction pressure between the coupling device and the prosthesis. When the prosthesis is in place at the desired site in the body, suction pressure is eliminated and the prosthesis is no longer fastened to the coupling device. In a further preferred embodiment of the invention the pressure is increased after the prosthesis is in place thereby apposing the flat member of the prosthesis to tissue at the desired site.

The apparatus according to the invention combines pure a mechanical part for delivering the prosthesis to the anastomosis site and a fluid driven part for fastening the coupling device to the prosthesis, optionally fastening the targeting tube to the organ and in a preferred embodiment pressing the prosthesis against the organ.

The various embodiments of the invention will now be described with reference to the attached drawings, where:

FIG. 5 is a perspective view of a fourth embodiment of the anastomosis prosthesis.

FIG. 6 is a longitudinal section of said fourth embodiment of anastomosis prosthesis along long axis of side-arm.

FIG. 7 is a perspective view of a fifth embodiment of the anastomosis prosthesis according to the present invention.

FIG. 8 is a longitudinal section of said fifth embodiment of anastomosis prosthesis along long axis of side-arm.

DETAILED DESCRIPTION OF A PREFERRED EMBODIMENT OF THE INVENTION

Anastomosis Prosthesis

Figure 1:
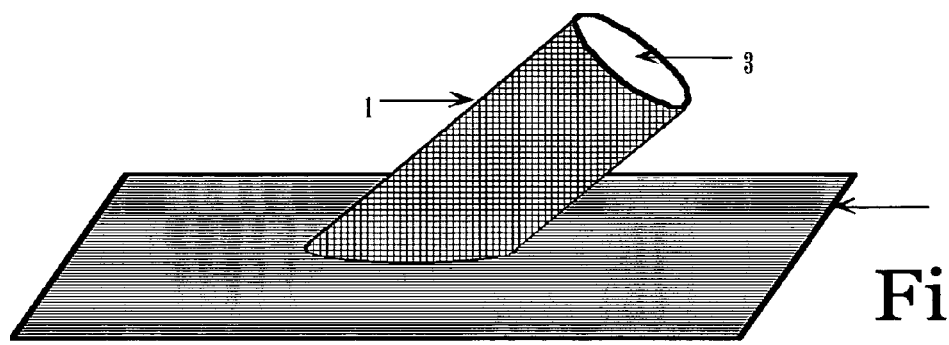
FIG. 1 is a perspective view of a first embodiment of the anastomosis prosthesis.
Figure 2:
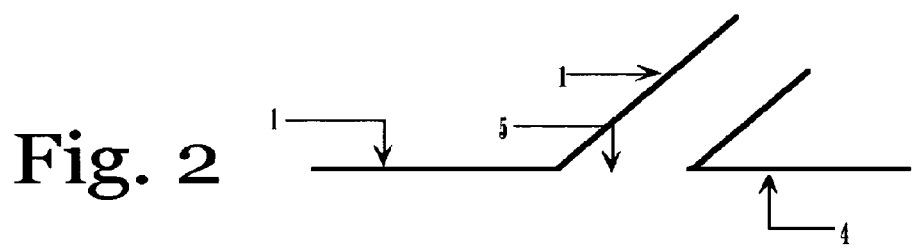
FIG. 2 is a longitudinal section of the embodiment in FIG. 1 along long axis of side-arm.

FIGS. 1 and 2 show a first embodiment of the anastomosis prosthesis for use in the present invention. In this embodiment the prosthesis comprises a tubular member (side-arm) 1 that is attached to a flat, pliable sheet (attachment member) 2 at an acute angle or at 90°, such that the luminal or inner surface 3 of the side-arm 1 is continuous with the far surface (attachment surface) 4 of the attachment member 2, that is the surface of the attachment member facing the second organ. An opening (ostium) 5 in the attachment member 2 matches the cross-sectional area of the lumeni of the side-arm 1.

The attachment surface 4, or the luminal surface 3, or both are preferably lined with a biocompatible adhesive, or one or multiple pharmacologic agents or both.

Figure 3:
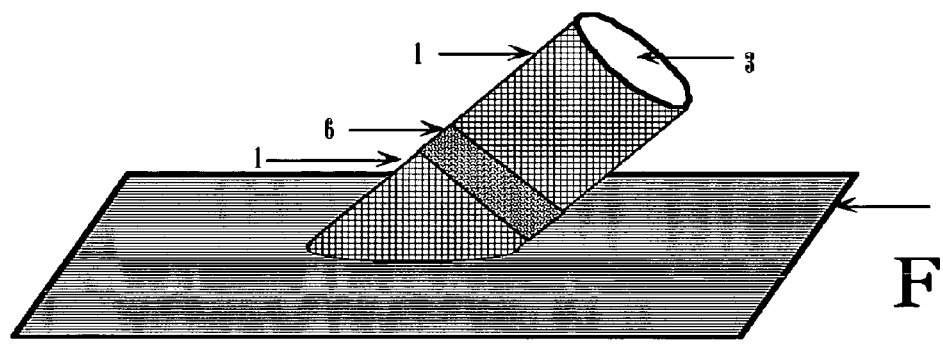
FIG. 3 is a perspective view of a second embodiment of the anastomosis prosthesis.

FIG. 3 shows a second embodiment of the prosthesis, wherein the end of the side-arm 1 continuous with the attachment member 2 is reinforced with a metal collar 6, that may have thermodynamic shape-memory.

Figure 4:
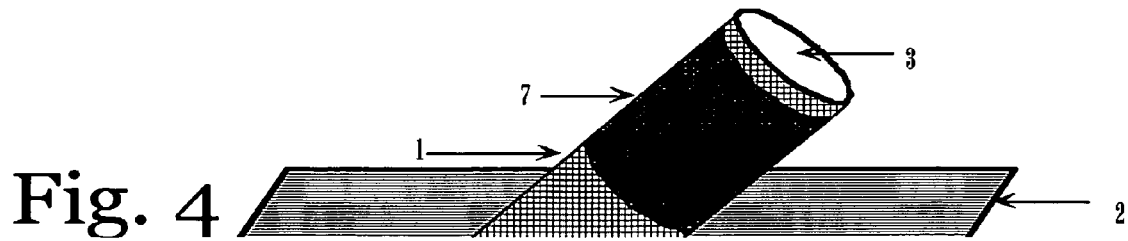
FIG. 4 is a perspective view and a partial cut of a third embodiment of the anastomosis prosthesis.

FIG. 4 shows a third embodiment of the prosthesis wherein the side-arm 1 is reinforced with a cylindrical mesh 7 of a metal with thermodynamic shape-memory.

FIGS. 5 and 6 show a fourth embodiment of the prosthesis. In this embodiment, the side-arm 1 is parallel to the attachment member 2, and has a side-hole 8, that is circumferentially continuous with the ostium or opening 5 in the attachment member 2.

FIGS. 7 and 8 show a fifth embodiment of the prosthesis. Here, a second tubular member (apparatus inlet) 9 is connected to the side-arm 1, such that the opening (apparatus port) 10 between the side-arm 1 and the apparatus inlet 9 projects on the ostium 5 along the long axis of the apparatus inlet 9.

The attachment member 2 is preferably provided with visual markers to help align the prosthesis satisfactorily with the organ.

Apparatus and Coupling Device

Figure 9:
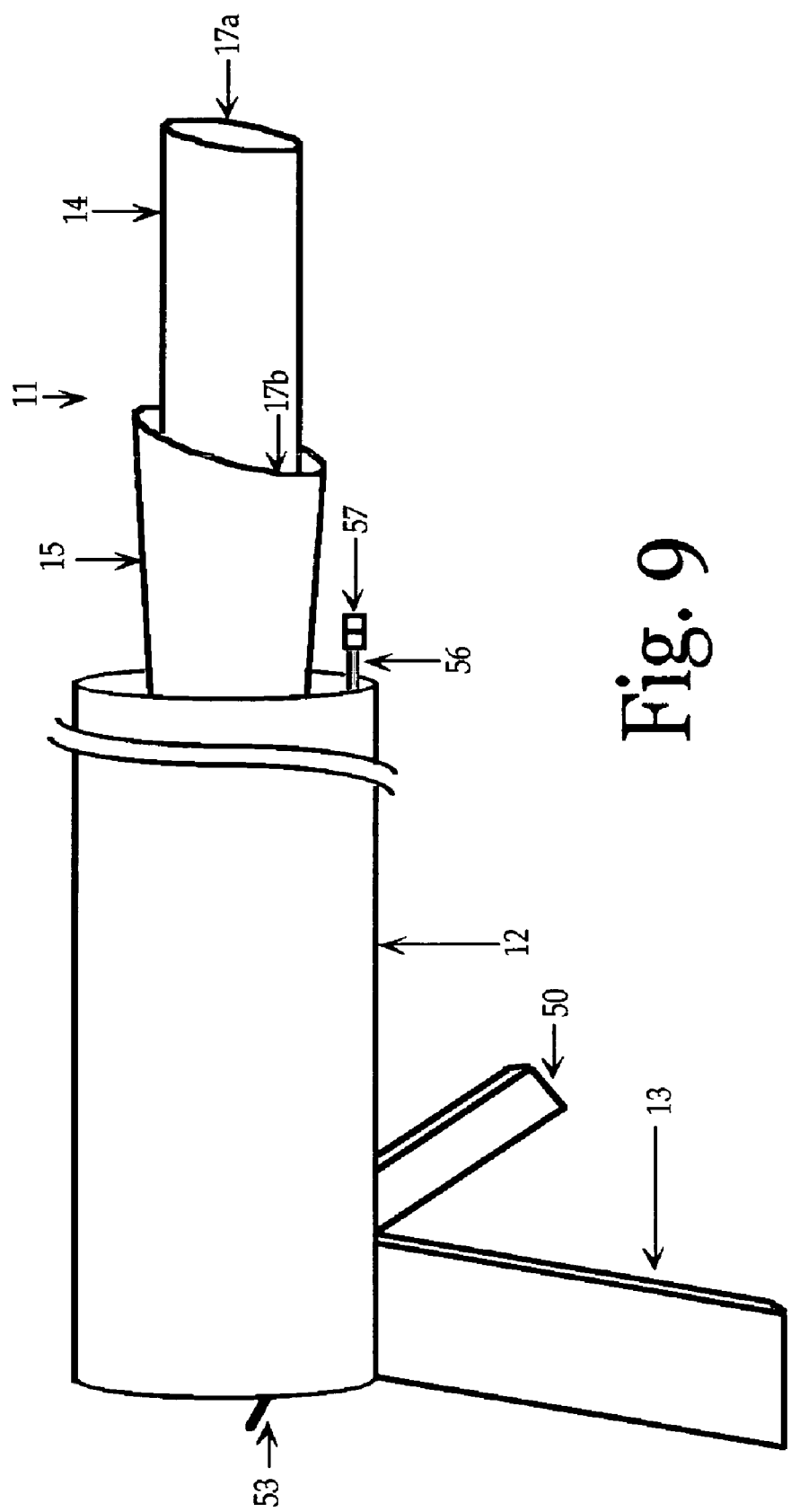
FIG. 9 is a perspective view of an embodiment of apparatus according to the invention.

FIG. 9 shows a first embodiment the apparatus according to the invention. It comprises an elongated part 11 with an assembly to carry the anastomosis prosthesis, and an outer casing (body) 12 incorporating a hand grip 13, that contains the trigger to deploy the anastomosis prosthesis and a flow control lever 53 for controlling flow in and out of the apparatus. FIG. 9 shows also a fluid connecting device or female device 57 for connection between the apparatus and the prosthesis coupling device.

The elongated part 11 includes two sliding coaxial tubular members, an inner targeting-tube 14, and the deployment tube 15. The targeting tube 14 permits placement of the apparatus on the right position on one of the organs to be anastomosed, while the deployment tube 15 carries the prosthesis and moves it into place on said organ.

Figure 10:
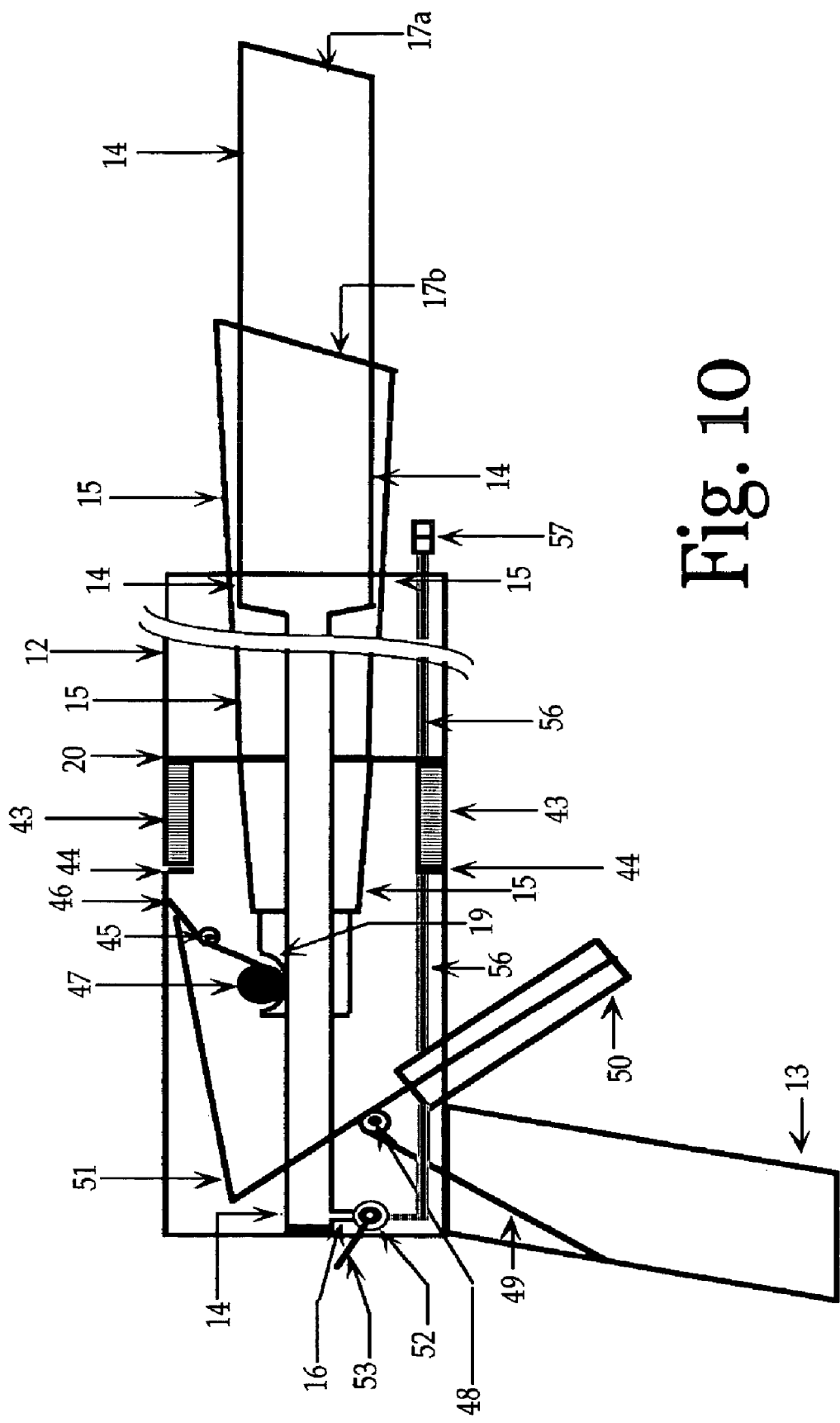
FIG. 10 is a longitudinal section of said embodiment of the apparatus.

Referring now to FIG. 10 that shows a longitudinal section of the apparatus, the targeting-tube 14 runs the length of the apparatus and has a side-arm 16 near one end, this side-arm establishes a connection between a flow control valve 52 and the targeting tube. The flow control valve 52 as will be described later is adapted for coupling to a suction apparatus and a suction pressure can thus be transmitted vil side-arm 16 to the targeting tube 14. For this purpose the end of the targeting-tube 14 near the side-arm 16 is fixed to the body 12 such that the attachment is impervious to the passage of air. The other end of the targeting-tube 14 protrudes from body 12, and its free-edge 17a is perpendicular to the longitudinal axis of the tube 14 or makes an acute angle with it.

Figure 11:
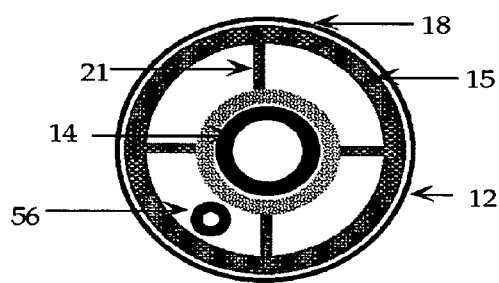
FIG. 11 is a transverse cross section (through spring compression plate) of preferred (first) embodiment of instrument.

The deployment tube 15 is shorter in length than the targeting-tube 14 and the free edge of its protruding end 17b is substantially congruent with the corresponding free edge 17a of the targeting-tube 14. At the opposite end of the deployment tube, an upwards-facing circular recess 19 is present. Forward to the recess 19, the deployment tube 15 has a coaxial collar (spring-compression plate) 20 that can be seen in further detail in FIG. 11, which shows how compression plate 20 is fixed to the deployment tube 15 by two or more radial struts 21.

The body of apparatus 12 has the shape of a flattened cylinder which is closed at one end. An angulated extension near the closed-end serves as the hand-grip 13. A helical compression spring 43 is coaxially mounted between a narrow collar oil the inner surface of the body (spring-retention collar) 44, and the spring-retention plate 20 of the deployment tube 15, distracting the retention collar 44 from the retention plate 20. Behind the spring-retention collar, is a pivot pin 45 supporting a substantially linear member (pivoting lever) 46. Fixed to the lower end of the pivoting lever 46 is a spherical member (weighting sphere) 47, whose weight applies counter-clockwise torque on the pivoting lever 46. The other end of the pivoting lever is in contact with the inner surface of the body 12 and is thereby restrained from free counter-clockwise rotation. Hinged via a pivot pin 48 to a pair of brackets in the hand-grip 13, and biased by a torsion spring 49, is a lever designed to accommodate the fingers (trigger) 50. A <<L?> shaped member, (trip lever) 51 extends from the trigger 50 within the lumen of the body 12, in the direction of the upper end of the pivoting lever 46. The body 12 is provided with a 3-port, 3-way valve 52, whose flow control lever 53 is accessible from outside the body 12 of the apparatus, the flow control lever 53 being the trigger of the fluid driven part of the apparatus.

Figure 12:
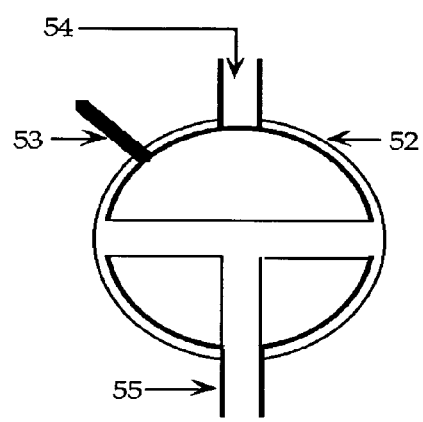
FIG. 12 is a cross-section (through first and second outlet ports) of a 3-port valve in a first position.
Figure 13:
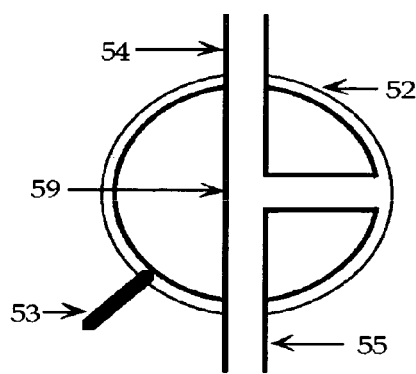
FIG. 13 is a cross-section (through first and second outlet ports) of the 3-port valve in FIG. 12 in a second position.
Figure 14:
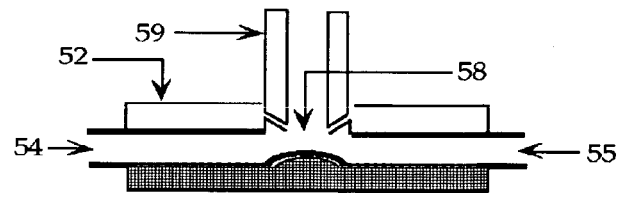
FIG. 14 is a longitudinal section (through first and second outlet ports) of the 3-port valve in FIG. 12 in the second position.

FIGS. 12, 13 and 14 show valve 52 in closer detail. One outlet 54 of the valve 52 is connected to the sidearm 16 of the targeting-tube 14 as stated before. Another outlet 55 of the valve 52 is connected to a flexible tube (primary suction tube) 56, which ends in the female counterpart 57 of the male component 34 of the tubing connection assembly that permits coupling of the coupling device to the prosthesis in a way that will be described in detail later. The female component 57 of the tubing connection assembly is fixed to the deployment 15 tube near its free edge 17b. The inlet 58 of the valve is continuous with an external plug (suction plug) 59 that is suitable for connecting to a suction apparatus.

The function of the embodiment of the apparatus described above will be explained later in the description.

Figure 15:
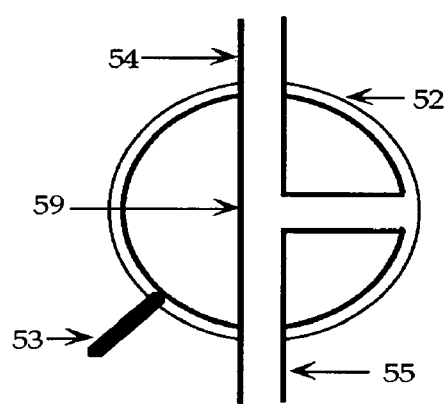
FIG. 15 is a cross-section of the coupling device through suction chambers.
Figure 16:
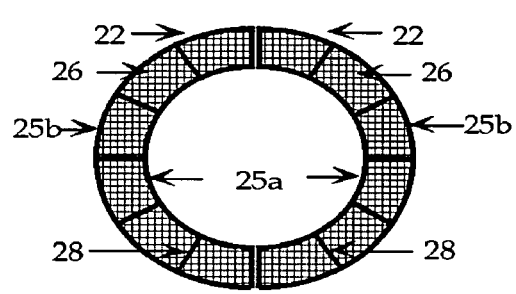
FIG. 16 is a cross-section of the coupling device through free edges.
Figure 17:
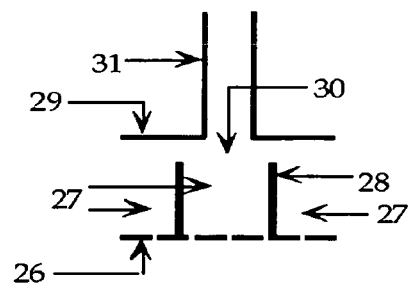
FIG. 17 is a longitudinal para-tangential section of the coupling device through three adjacent suction chambers.
Figure 18:
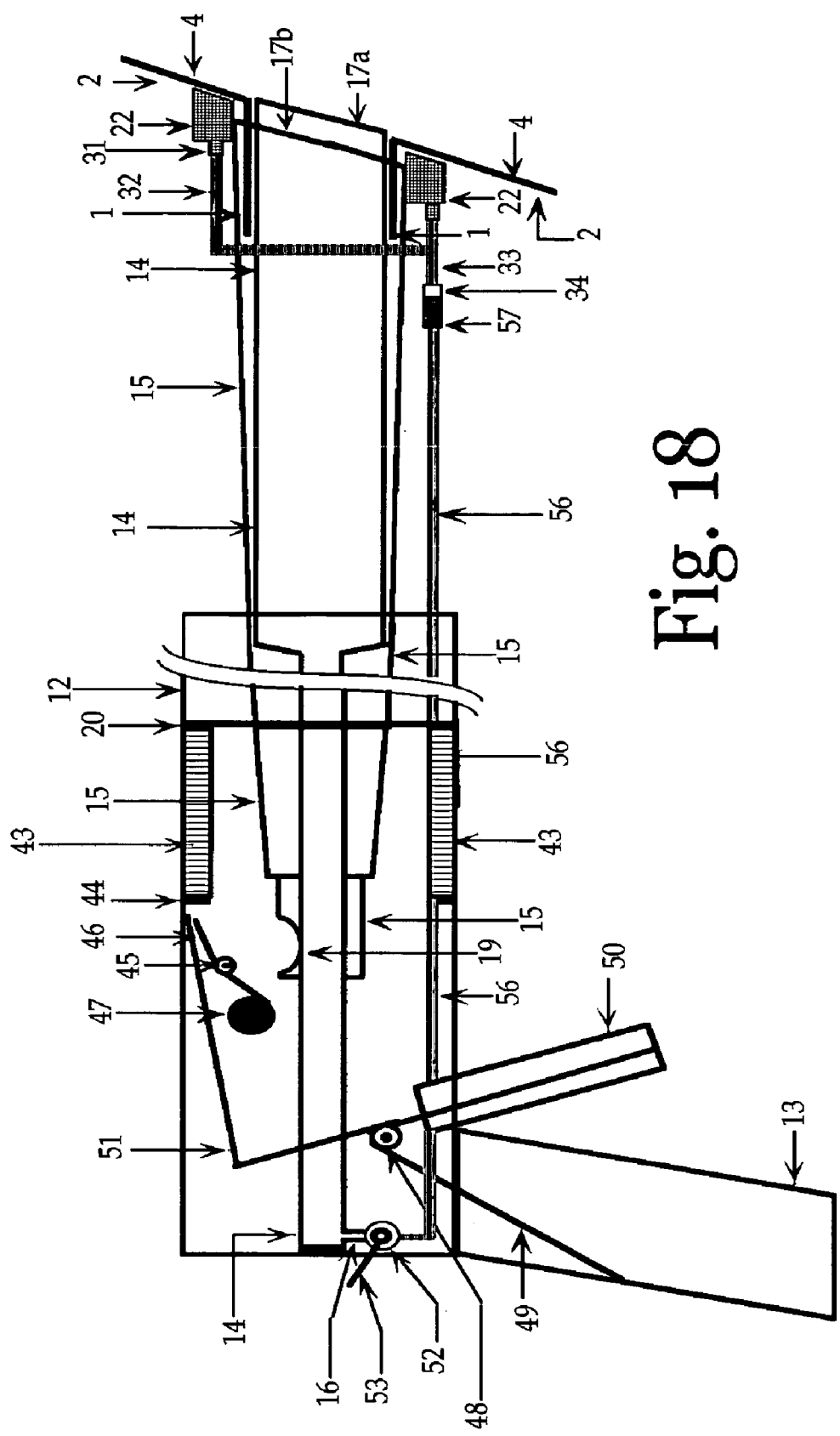
FIG. 18 is a longitudinal section of the apparatus, the coupling device and the prosthesis according to the invention and shows the fluid circuit.

FIG. 15 shows one embodiment of the coupling device according to the invention. This coupling device comprises a double-walled, substantially thimble-formed, ring-shaped member, comprising of at least one, and in this case of two ring sections or suction hoods 22, with similar radii of curvature. The coupling device can comprise more than two suction hoods 22 arranged in a circle as shown in the figure. Each suction hood 22 is divided into multiple suction chambers 27 by radial partition walls 28. FIGS. 15 and 16 show that each suction hood 22 has parallel inner 23 and outer 24 walls, said walls being connected on one edge 25a, 25b by a mesh 26 in a preferred embodiment of the invention. As can be seen in FIG. 17, which shows a section of a suction hood 22, each suction hood 22 comprises a roof 29 which forms a ring shaped channel 30 communicating with each suction chamber 27 and thus establishing fluid connection between each chamber 27. Roof 29 (and thus ring shaped channel 30) are in fluid connection with a tubing connection assembly for transmitting a suction pressure from a connecting device to chambers 27. Said tubing connection assembly is shown schematically in FIG. 18 and comprises a linear plug 31 (connection plug) protruding from the roof 29 of the suction hood 22 coupled to channel 30. To plug 31 is attached a tube (tertiary suction tube) 32.

The tertiary suction tubes from all suction hoods 22 of the ring shaped member open into a single tube (secondary suction tube) 33, which in turn ends in the male component 34 of the tube connection assembly. This male component 34 is the counterpart of the female component 57 mentioned with reference to FIGS. 9 and 10. The fluid circuit is thus described in its entirety. Its function is to transmit a suction pressure from a suction apparatus (not shown) to suction hoods 22 so that these exert a suction pressure on the anastomosis prosthesis and hold it in place on the deployment tube 15.

Figure 19:
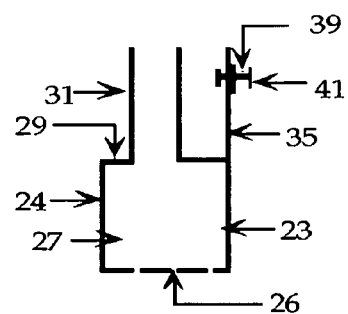
FIG. 19 is a longitudinal radial section of the coupling device through fixation screw and connection plug.
Figure 20:
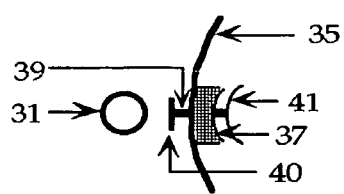
FIG. 20 is a cross-section through fixation screw of attachment plate of the coupling device.

The suction hoods 22 are mechanically fastened to deployment tube 15 by means of a fixation mechanism that will be described with reference to FIGS. 19–21 which cooperates with a fastening device in the apparatus, which fastening device will be described with reference to FIG. 23. FIG. 19 shows that at the apex of its curvature, the inner wall 23 of the suction hood 22 is continuous with a short rectangular plate (attachment plate) 35 that protrudes beyond the roof 29 of the hood 22. On the inner surface of the attachment plate 35 is a flat rectangular projection (offset block) 36. FIG. 20 shows the offset block 36 with a concave free surface 37.

Figure 21:
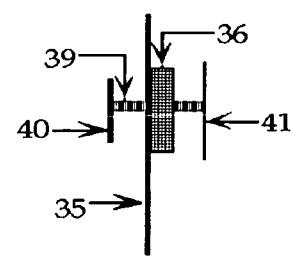
FIG. 21 is a longitudinal section of the coupling device through fixation screw.

FIG. 21 shows a first embodiment of the coupling device where a threaded fixation pin (fixation screw) 39 carrying a nut 40 passes perpendicularly through the attachment plate 35 and offset block 36. To the tip of the fixation screw 39 is attached a convex plate (fixation plate) 41, this figure shows the curvature of the attachment plate 35, offset block 36 and fixation plate 41.

Figure 22:
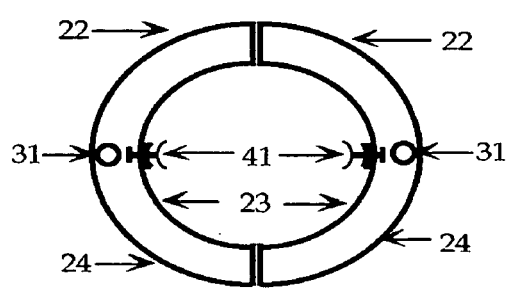
FIG. 22 is a cross-section of the coupling device through attachment plates.

FIG. 22 shows the ring shaped member comprising two suction hoods 22 and the relative positions of linear plug 31 for fluid connection, and the fixation mechanism comprising fixation plate 41, offset block 36, fixation pin 39 and nut 40.

Figure 23:
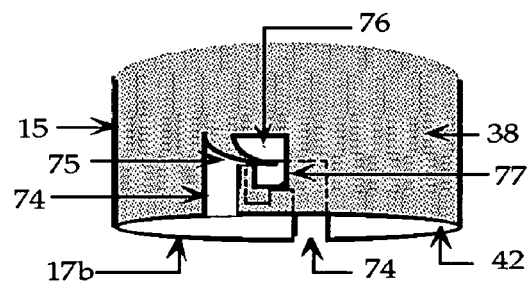
FIG. 23 is a perspective view of a first embodiment of free end of deployment tube.

FIG. 23 shows the edge 17b of deployment tube 15 in detail in a first embodiment of the apparatus. This figure shows the fastening device implemented as two or more short rectangular slots (fixation slots) 18 extending from the edge 17b which are arranged symmetrically around the circumference of the deployment tube 15. The aim of the fixation slots 18 is to provide a seat for introduction of fixation screw 39 in the coupling device for fastening the coupling device to the deployment tube 15.

Figure 24:
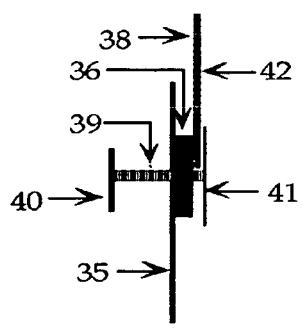
FIG. 24 is a longitudinal section (through fixation pin) of fixation plate of coupling device mounted on deployment tube.
Figure 25:
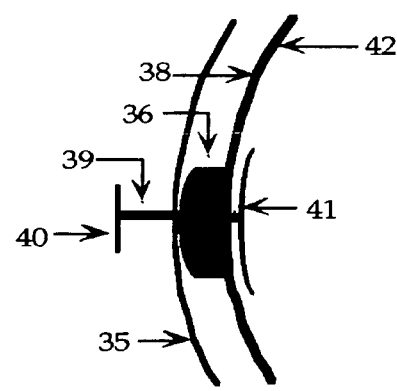
FIG. 25 is a cross-section (through fixation pin) of fixation plate of coupling device hood mounted on deployment tube.

FIGS. 24 and 25 show in detail the relative placement of suction hood 22 and deployment tube 15. Offset block 36 and fixation plate 41 are meant to be tightened against the outer 42 and the inner 38 surface respectively of the deployment tube 15 in the apparatus by means of the pin 39. In other words, the free surface 37 on offset block 36 is adapted for apposing against the outer surface of deployment tube 15 while the convex plate 41 is adapted to appose against the inner surface 42 of deployment tube 15.

The concept behind the invention can be realised in several ways as expressed by the various alternative of the invention. These alternative embodiments will be described in detail later.

Use of the invention will be now described by means of an example of the coupling device and the apparatus as described above and with reference to FIGS. 22, 23, 24, 26 and 27.

Attachment of Suction Hood to Apparatus

Reference is now made to FIGS. 22 and 23 and 24. A suction hood 22 with an appropriate radius of curvature in relation to the anastomosis prosthesis to be implanted is attached to the deployment tube 15. In this example, the fixation screw 39 of the suction hood 22 is introduced into a fixation slot 18 of the deployment tube 15, and advanced until it reaches the floor 73 of the slot. The nut 40 on the fixation screw 39 is turned clockwise until the fixation plate 41 is closely apposed to the luminal surface 42 of deployment tube 15, thereby securing the suction hood to the deployment tube 15. More suction hoods 22 are attached symmetrically to the deployment tube 15, the total number depending on the number of available fixation slots 18 and size of the anastomosis prosthesis.

Implantation of Anastomosis Prosthesis

Figure 26:
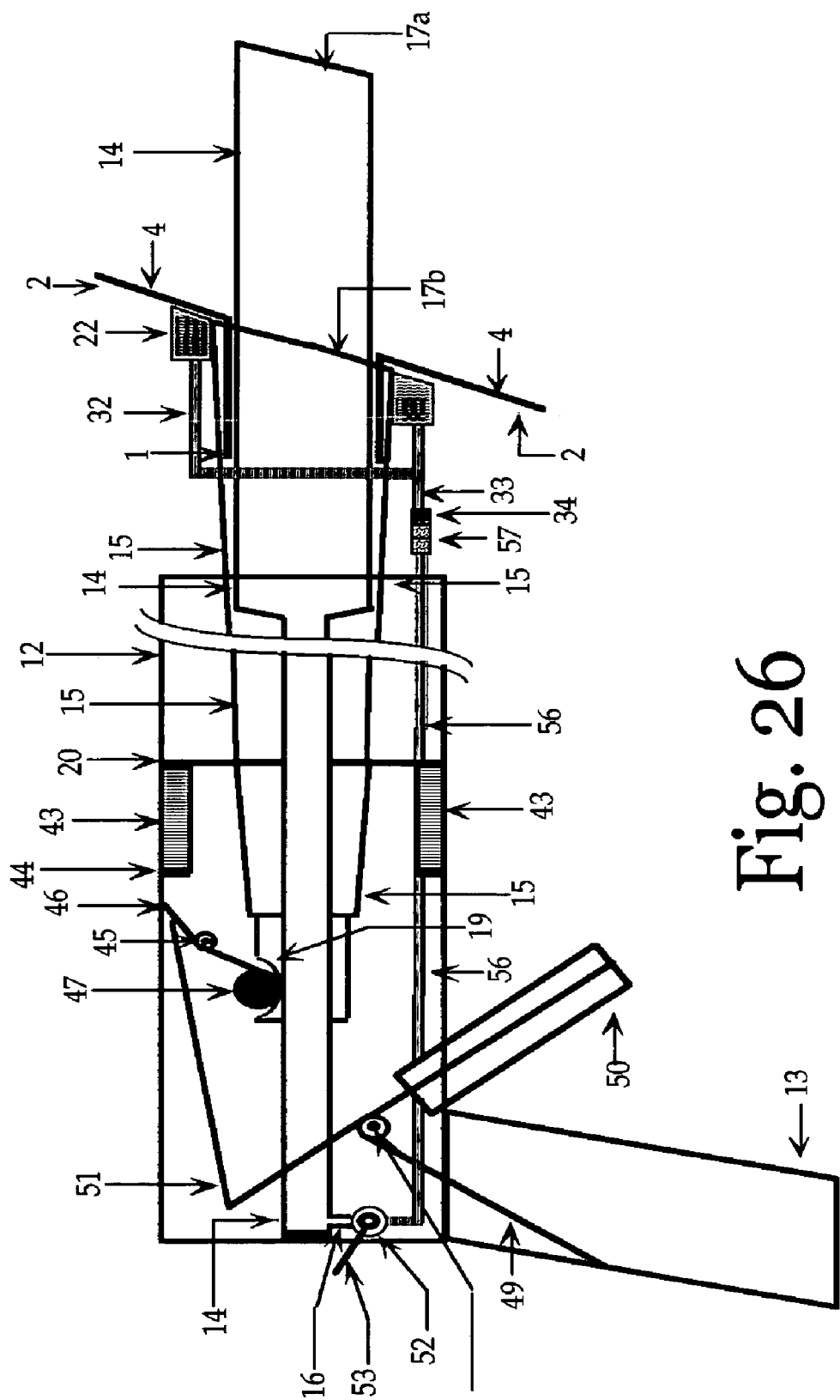
FIG. 26 is a longitudinal section of a preferred embodiment of the apparatus carrying two suction hoods.
Figure 27:
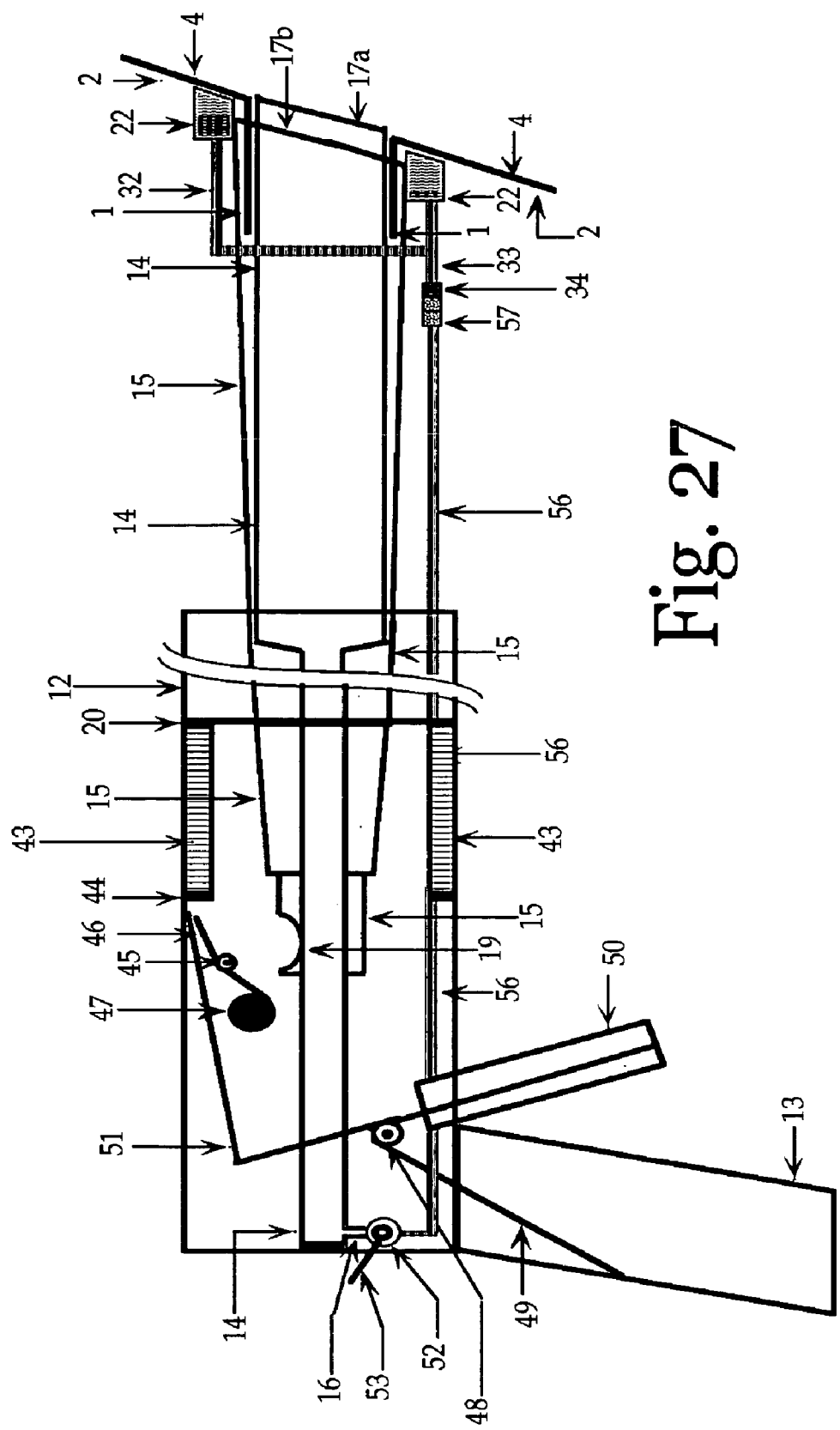
FIG. 27 is a longitudinal cross-section of a preferred embodiment of the apparatus (carrying two suction hoods) with trigger pressed.

Reference will now be made to FIGS. 7, 26 and 27. After the required number of suction hoods 22 are fixed to the deployment tube 15, the tertiary suction tubes are connected to the secondary suction tube 33, and the latter is mated with the primary suction tube 56, the apparatus is cocked by manually drawing the deployment tube 15 towards the body 12 of the apparatus till the weighting sphere 47 engages the circular recess 19 (FIG. 26). A suction apparatus is connected to the 5 suction plug 59 (not shown) on the 3-port valve 52. The targeting-tube 14 is introduced into the side-arm 1 or apparatus inlet 9 of an anastomosis prosthesis (FIG. 7), and advanced till the suction hoods 22 symmetrically abut the attachment member 2 of the prosthesis. The flow control lever 53 of the valve 52 is placed in position I (FIG. 26), establishing a channel between the suction apparatus and the primary suction tube 56. The suction apparatus is powered up creating negative pressure in the suction chambers 28, securing the anastomosis prosthesis to the apparatus. The free edge 17a of the targeting-tube 14 is placed at the desired site on the organ to be anastomosed, and aligned as appropriate. If deemed appropriate, an imaging device or a flow-measurement device may be introduced into the targeting-tube 14 through an inlet 70 (not shown) and the relevant data collected to confirm that the site selected for anastomosis is suitable. The flow-control lever 53 is placed in position II (FIG. 27), creating an open fluid circuit between the suction apparatus and the targeting-tube 14. Negative pressure is established in the targeting-tube 14, securing it to the organ. A biocompatible adhesive is applied to the tissue surfaces around the free edge 17a of the targeting-tube 14. This step may be skipped if the attachment surface 3 of the attachment member 2 is lined with an adhesive. The trigger 50 is pressed, rotating the trip lever 51 forwards (FIG. 27). The tip of the trip lever 51 rotates the pivoting lever 46, elevating weighting sphere 47. The compression spring 43 expands, driving the deployment tube 15 forwards, and apposing the attachment surface 4 of the anastomosis prosthesis to the organ to be anastomosed and the surrounding tissues. The flow-control lever 53 is placed in position I, and the pressure in the suction circuit is lowered further. After a firm adhesive bond has been established between the anastomosis prosthesis and the tissues, the suction apparatus is powered down. The flow control 53 lever is placed in position II, allowing the pressure in the suction circuit to return to atmospheric levels. The apparatus is removed from the body, leaving the anastomosis prosthesis attached to the organ.

Alternative Embodiments of the Invention and Their Use

In an embodiment of the apparatus the suction hood 22 does not have a mesh 26. The advantage of this embodiment is that the absence of a mesh increases the suction force that is applied to the anastomosis prosthesis.

Figure 28:
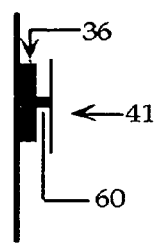
FIG. 28 is a longitudinal section of the attachment plate through fixation pin in a second embodiment of the coupling device.
Figure 29:
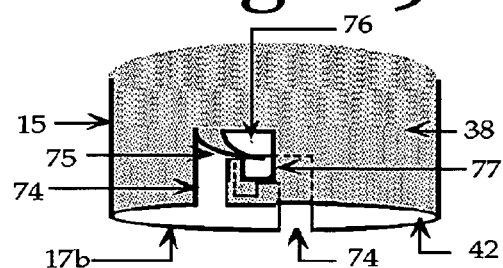
FIG. 29 is a perspective view of the free end of the deployment tube in a second embodiment of the apparatus.

FIG. 28 shows a second embodiment of the coupling device where the fixation mechanism comprises a short pin (fixation pin) 60 with the fixation plate 41 at its tip. FIG. 29 shows a second embodiment of the apparatus where the fastening device is implemented as fixation slots 18 comprising a long limb 74 for insertion of a fixation pin, a fixation fluke 74 to lock the fixation pin in place, a transverse limb 76 and a short limb 77. In this case, the fixation pin 60 is introduced into the long limb 74 of the fixation slot 18, and advanced till the fixation fluke 75 is displaced, opening the transverse limb 76 of the fixation slot 18. The suction hood 22 is revolved so that the fixation pin 60 advances along the transverse limb till it reaches the short limb 77 of the fixation slot 18. The suction hood 22 is released allowing the fixation fluke 75 to push the fixation pin 60 into the short limb 77 of the fixation slot 18, securing the suction hood 22 to the deployment tube 15.

Figure 30:
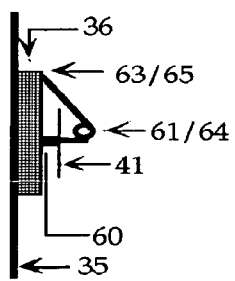
FIG. 30 is a longitudinal section of the attachment plate through torsion spring in a third embodiment of the coupling device.
Figure 31:
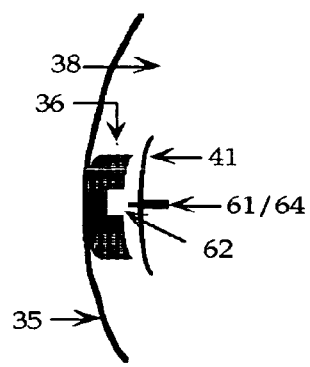
FIG. 31 is a cross-section of the attachment plate along the free end of the torsion spring in said third embodiment.
Figure 32:
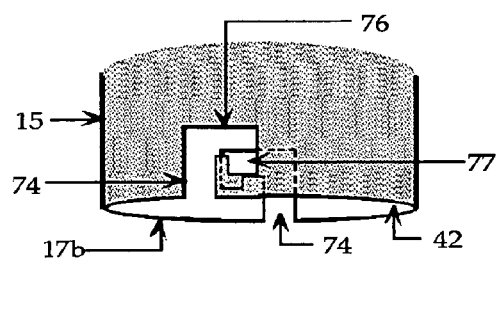
FIG. 32 is a perspective view of the free end of deployment tube in a third embodiment of the apparatus.
Figure 33:
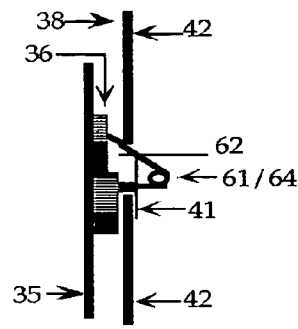
FIG. 33 is a longitudinal cross-section (through torsion spring) of fixation plate of a suction hood mounted on the deployment tube.

FIGS. 30 and 31 shows a third embodiment of the coupling device where the fixation mechanism comprises fixation plate 41 and perpendicularly attached to this one limb of a torsion spring 61. The torsion spring 61 is coplanar with the long axis of the deployment tube 15. The offset block 36 in this embodiment has a linear groove 62 to accommodate the free end 63 of the torsion spring 61. FIG. 32 shows a third embodiment of the apparatus. In this embodiment, the fixation slots 18 have a long limb 74, a traverse limb 76 and a short limb 77. In use, the fixation pin 60 is introduced into the long limb 74 of the fixation slot 18 and advanced till it reaches the transverse limb 76 of the slot 18. The suction hood 22 is revolved so that the fixation pin 60 advances along the transverse limb 76 till it reaches the short limb 77 of the fixation slot 18. The suction hood 22 is released allowing the torsion spring 61 to push the fixation pin 60 into the short limb 77 of the fixation slot 18, securing the suction hood 22 to the deployment tube 15 (FIG. 33).

In a fourth embodiment of the coupling device (FIGS. 30, 31) the fixation mechanism comprises a resilient wire 64 bent at an acute angle. One end of the wire 64 is perpendicularly attached to the fixation plate 41, such that both limbs lie in a plane parallel to the long axis of the deployment tube 15. The offset block 36 has a linear groove 62 to accommodate the free end 65 of the resilient wire. In use, the fixation pin 60 is introduced into the long limb 74 (FIG. 32) of the fixation slot 18 and advanced until it reaches the transverse limb 76 of the slot 18. The suction hood 22 is revolved so that the fixation pin 60 advances along the transverse limb 76 till it reaches the short limb 77 of the fixation slot 18. The suction hood 22 is released allowing the free limb 65 of the resilient wire 64 to snap back to its original orientation, pushing the fixation pin 60 into the short limb of the fixation slot 18, securing the suction hood 22 to the deployment tube 15 (FIG. 33).

In case of the embodiment of the anastomosis prosthesis shown in FIGS. 5 and 6, a modified version of the implantation procedure is used. The apparatus is not cocked. The anastomosis prosthesis is manually apposed against the end of the targeting-tube 14 such that the suction hoods 22 are symmetrically apposed to the attachment member 2, before the anastomosis prosthesis is hypobarically secured to the deployment tube 15 as explained above. The targeting-tube 14 is not hypobarically secured to the organ to be anastomosed. Nor is the anastomosis prosthesis mechanically deployed by pressing the trigger 50. Instead the anastomosis prosthesis is placed at the desired site, prior to reducing the pressure further in the suction circuit to ensure tight apposition between the attachment surface 4 of the anastomosis prosthesis and the underlying tissues.

Figure 34:
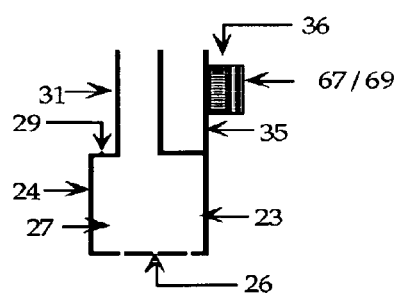
FIG. 34 is a longitudinal radial section (through fixation pin) of a fifth and a sixth embodiment of the coupling device mounted on the deployment tube.
Figure 35:
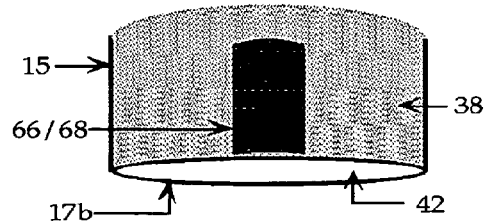
FIG. 35 is a perspective view of the free end of deployment tube of a fifth embodiment of the apparatus.

FIG. 34 shows a fifth embodiment of the coupling device where the suction hood 22 lacks a fixation screw 39 with plate 41. Instead, a polymer patch carrying multiple small, flexible, hooks (hook patch) 67 on its surface is bonded to the offset block 36. FIG. 35 shows a fourth embodiment of the apparatus, where the fastening means are implemented by providing the outer surface 38 of the deployment tube 15 with two or more polymer patches carrying multiple small loops on its surface (loop patch) 66. The loop patches 66 are arrayed symmetrically around the circumference in the vicinity of the free edge 17*b* of the deployment tube 15. In use, the hook patch 67 on the offset block 36 is manually apposed to a loop patch 66 on the deployment tube 15, allowing the hooks to engage the loops, securing the suction hood 22 to the deployment tube 15.

In a sixth embodiment of the coupling device (FIG. 34) a flat magnet 69 is fixed to the offset block 36 of the suction hood 22. In a fifth embodiment of the apparatus (FIG. 35), the outer surface 38 of the deployment tube 15 is provided with two or more ferromagnetic patches 68. The ferromagnetic patches 68 are arrayed symmetrically around the circumference of the deployment tube 15, in the vicinity of its free edge 17*b*. In a preferred embodiment the surface of the magnet 69 has a pattern on it in bas relief which complements the pattern engraved on the ferromagnetic patch 68. In use, the magnet 69 on the offset block 36 is manually apposed to a ferromagnetic patch 68 on the deployment tube 15, securing the suction hood 22 to the deployment tube 15. In this embodiment of the apparatus, the magnet 69 on the offset block is manually apposed to a ferromagnetic patch 68 on the deployment tube 15, ensuring that the each ridge on the magnet 69 engages the corresponding groove on the ferromagnetic patch 68.

In a preferred embodiment of the apparatus the targeting-tube is provided with a inlet for the introduction of imaging or flow measurement devices. The inlet may advantageously incorporate a valve for creating an airtight seal irrespective of whether or not an imaging or flow-measurement device is placed in the targeting-tube.

Figure 36:
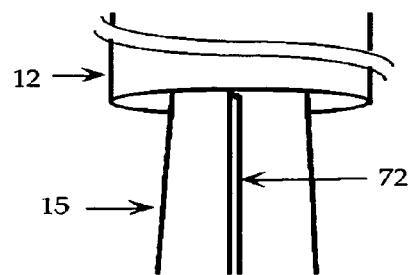
FIG. 36 is a perspective view of free end of the deployment tube in another embodiment of the apparatus.

FIG. 36 shows an embodiment of the apparatus, wherein the deployment tube 15 is provided with two or more long narrow slits 72 that are parallel to the long axis of the tube 15. The slits 72 are symmetrically arrayed around its circumference. These long narrow slits allow reversible splaying of the free end of the deployment tube 15 making it possible to attach coupling devices with radii of curvature substantially larger than the radius of the deployment tube 15 itself. This feature eliminates the need to dimensionally match the deployment instrument to the anastomosis prosthesis being deployed.

The combination of pressure-mediated attachment and release of the anastomosis prosthesis, with its mechanical deployment offers a number of advantages of relevance to the surgeon. The anastomosis prosthesis can be reversibly, yet securely, attached to the deployment instrument without the risk of damage associated with mechanical fixation. Release of the prosthesis after deployment does not involve the manipulation of movable members that may traumatise the target organ. The mechanical deployment mechanism allows for rapid, reliable single-handed delivery of the prosthesis to the target. As the coupling device carrying the prosthesis is detachable from the deployment instrument, the latter can be used with anastomosis prostheses of a wide range of sizes simply by matching the radius of curvature of the coupling device to the size of the anastomosis prosthesis.

Thus the invention allows accurate and reliable delivery of an anastomosis prosthesis to the chosen site on the target organ, which is a vital prerequisite to the performance of externally-supported non-sutured anastomosis.

The invention claimed is:

1. An instrument for preparing a hollow organ for anastomosis to another hollow organ, comprising:
   (a) an implantable prosthesis with a first tubular member attached to a flat pliable member with an opening, wherein,
      the first tubular member has a first free end and a second end, and,
      the first tubular member and the pliable member are connected such that the luminal surface of the first tubular member is continuous with the far surface of the flat member, and,
      the opening in the flat member matches the cross-sectional area of the lumen of the first tubular member, and,
   (b) an instrument comprising a coupling device for securely holding said prosthesis, and a deployment apparatus for delivering said prosthesis to a desired location, wherein,
      (i) said coupling device comprising a double-walled ring shaped member, a tubing connection assembly, and a first fixation mechanism, wherein,
         1. said ring shaped member is provided with radial partitions defining a plurality of chambers, with each chamber having a first end and a second end such that, each of said chambers is luminally continuous with all other said chambers, through its said first end, and each of the chambers is open to the atmosphere through its said second end, and,
         2. the first tubing connection assembly is in fluid connection with all of the said chambers, and,
         3. the first fixation mechanism allows said ring-shaped member to be fastened to said deployment apparatus, and
      (ii) said deployment apparatus comprising a first tube with a free edge and a coaxial outer second tube with a free edge, a flow control valve, a mechanism for displacing the second tube with respect to the first tube, and a trigger for activating said mechanism, wherein,
         1. said first tube is provided with a side-arm, said side-arm being luminally continuous with the first tube,
         2. said second tube is provided with a second fixation mechanism that cooperates with the first fixation mechanism, of the coupling device and,
         3. said flow control valve has an inlet, a first outlet, a second outlet, and a flow control lever, wherein,
            ($\alpha$) said inlet is adapted for connection to a suction apparatus, and,
            ($\beta$) said first outlet is coupled to the side-arm of the first tube, and,
            ($\chi$) said second outlet is coupled to a fluid connection device, the said fluid connection device being adapted for connection to a the tubing connection assembly.

2. A device according to claim 1, wherein the ring shaped member is comprised two or more radially arrayed sections.

3. A device according to claim 1, wherein the first fixation mechanism is comprised of an attachment plate with a rectangular projection, and a pin, wherein,
   (a) the attachment plate and the rectangular projection are each provided with at least one perforation, and (b) the pin is threaded, and has a first end and a second end, and provided with a nut at or near the first end, and a fixation plate at or near the second end.

4. A device according to claim 3, wherein the pin is not threaded.

5. A device according to claim 4, wherein the first fixation mechanism is provided with a torsion spring and the rectangular projection is provided with a groove, wherein,
 (a) the torsion spring has a first limb and a second limb, and,
 (b) the first limb is attached to the fixation plate, and the second limb is accommodated in the groove on the rectangular projection.

6. A device according to claim 4, wherein the first fixation mechanism is provided with a bent resilient wire, wherein,
 (a) the bent resilient wire has a first limb and a second limb, and,
 (b) the first limb is attached to the fixation plate, and the second limb is accommodated in the groove on the rectangular projection.

7. A device according to claim 1, wherein the first fixation mechanism is comprised of an attachment plate with a rectangular projection, wherein to said rectangular projection is attached:
 (a) a first hook patch or a first array of hook patches, or,
 (b) a first loop patch or a first array of loop patches, or,
 (c) a first hook patch or a first array of hook patches, and a first loop patch or a first array of loop patches.

8. A device according to claim 1, wherein the first fixation mechanism is comprised of an attachment plate with a rectangular projection, wherein to said rectangular projection is attached:
 (a) a first magnet or a first array of magnets, or,
 (b) a first ferromagnet or a first array of ferromagnets, or,
 (c) a first magnet or a first array of magnets, and a first ferromagnet or a first array of ferromagnets.

9. A device according to 1, wherein a mesh is attached to the free ends of the chambers of the coupling device.

10. A device according to claim 1, wherein the second attachment mechanism comprise at least one slot extending from the free edge of the second tube.

11. A device according to claim 10, wherein the slot comprises a long limb, a transverse limb, and a short limb.

12. A device according to claim 10, wherein the slot comprises a long limb, a fluke, a transverse limb and a short limb.

13. A device according to claim 1, wherein:
 (a) the second tube is provided with a second hook patch or a second array of hook patches, wherein the second hook patch or the second array of hook patches cooperate repectively with the first loop patch or the first array of loop patches found on the first attachment mechanism, or,
 (b) the second tube is provided with a second loop patch or a second array of loop patches, wherein the second loop patch or the second array of loop patches cooperate repectively with the first hook patch or the first array of hook patches found on the first attachment mechanism, or,
 (c) the second tube is provided with a second hook patch or a second array of hook patches, and a second loop patch or a second array of loop patches, wherein the second hook patch or the second array of hook patches and the second loop patch or the second array of loop patches cooperate respectively with the first loop patch or first array of loop patches, and the first hook patch or the first array of hook patches, such that each loop patch cooperates with a hook patch and vice versa.

14. A device according to claim 1, wherein:
 (a) the second tube is provided with a second ferromagnet or a second array of ferromagnets, wherein the second ferromagnet or the second array of ferromagnets cooperate repectively with the first magnet or the first array of magnets found on the first attachment mechanism, or,
 (b) the second tube is provided with a second magnet or a second array of magnets, wherein the second loop magnet or the second array of magnets cooperate repectively with the first ferromagnet or the first array of ferromagnets found on the first attachment mechanism, or,
 (c) the second tube is provided with a second ferromagnet or a second array of ferromagnets, and a second magnet or a second array of magnets, wherein the second ferromagnet or the second array of ferromagnets and the second magnet or the second array of magnets cooperate respectively with the first magnet or first array of magnets, and the first ferromagnet or the first array of ferromagnets, such that each ferromagnet cooperates with a magnet and vice versa.

15. A device according to claim 1, wherein the first tube is provided with an inlet.

16. A device according to claim 15, wherein the inlet is provided with a valve.

17. A device according to claim 1, wherein the second tube is provided with two or slits extending from the free edge of the second tube, characterized by said slits being oriented substantially parallel to the long axis of the second tube.

18. A device according to claim 1, wherein the far surface of the flat member or the luminal surface of the first tubular member or both incorporate an adhesive lining or one or more pharmcaologic agents or both adhesive and one or more pharmacologic agents.

19. A device according to claim 1, wherein the second end of the first tubular member is reinforced with a collar.

20. A device according to claim 19, wherein the collar exhibits shape memory.

21. A device according to claim 1, wherein the first tubular member is reinforced with a mesh.

22. A device according to claim 21, wherein the mesh exhibits shape memory.

23. A device according to claim 1, wherein the first tubular member member lies parallel to the flat member, and said tubular member has a first side hole that is circumferentially contnuous with the opening in the flat member.

24. A device according to claim 23, wherein a second tubular member is attached to the first tubular member, such that:
 their lumina are contunuous at a second side hole of the first tubular member, and,
 the first side hole of the first tubular member is spatially a projection of the second side hole of the first tybular along the long axis of the second tubular member.

* * * * *